United States Patent
Lee et al.

(10) Patent No.: US 8,080,389 B2
(45) Date of Patent: Dec. 20, 2011

(54) **AUTO-INDUCIBLE SODIUM PHOSPHATE SYMPORTER PROMOTER FROM *PICHIA PASTORIS* AND METHOD FOR PRODUCING RECOMBINANT PROTEIN USING IT**

(75) Inventors: Hong Weon Lee, Daejeon (KR); Jung Oh Ahn, Daejeon (KR); Joon Ki Jung, Daejeon (KR); Eui Sung Choi, Daejeon (KR); Chun Suk Kim, Daejeon (KR); Eun Gyo Lee, Daejeon (KR); Ji Yeon Hong, Daejeon (KR); Hyeok Won Lee, Daejeon (KR); Myoung Soo Park, Daejeon (KR)

(73) Assignee: Korea Research Insitute of Bioscience and Biotechnology, Daejeon (KR)

( * ) Notice: Subject to any disclaimer, the term of this patent is extended or adjusted under 35 U.S.C. 154(b) by 521 days.

(21) Appl. No.: 12/294,511

(22) PCT Filed: Aug. 7, 2006

(86) PCT No.: PCT/KR2006/003096
§ 371 (c)(1),
(2), (4) Date: Jan. 12, 2009

(87) PCT Pub. No.: WO2007/117062
PCT Pub. Date: Oct. 18, 2007

(65) Prior Publication Data
US 2010/0279345 A1    Nov. 4, 2010

(30) Foreign Application Priority Data
Apr. 12, 2006 (KR) .................. 10-2006-0033064

(51) Int. Cl.
*C07H 21/04* (2006.01)
*C12N 15/63* (2006.01)
*C12N 1/19* (2006.01)
(52) U.S. Cl. ............... 435/69.1; 435/254.2; 435/320.1; 435/325; 536/24.1
(58) Field of Classification Search .................. None
See application file for complete search history.

(56) References Cited

U.S. PATENT DOCUMENTS
7,816,509 B2 * 10/2010 Lee et al. .................. 536/24.1

OTHER PUBLICATIONS

Waterham, H.R., et. al.: "Isolation of the *Pichia pastoris* glyceraldehyde-3-phosphate dehydrogenase gene and regulation and use of its promoter"; Gene, vol. 186(1), pp. 37-44 (Feb. 20, 1997).
Menendez, J., et. al.: "The ICL1 gene of *Pichia pastoris*, transcriptional regulation and use of its promoter"; Yeast, vol. 20(13), pp. 1097-1108 (Oct. 15, 2003).
Resina, D., et. al.: "Expression of a *Rhizopus oryzae* lipase in *Pichia pastoris* under control of the nitrogen source-regulated formaldehyde dehydrogenase promoter"; Journal of Biotechnology, vol. 109(1-2), pp. 103-113 (Apr. 8, 2004).
Martinez, P., et. al.: "Identification, cloning and characterization of a derepressible Na+-coupled phosphate transporter in *Saccharomyces cerevisiae*"; Molecular & General Genetics, vol. 258(6), pp. 628-638 (1998).
International Search Report and Written Opinion prepared by the Korea Intellectual Property Office on Jan. 5, 2007 for PCT/KR2006/003096; Applicant, Korea Research Institute of Bioscience and Biotechnology.

* cited by examiner

*Primary Examiner* — Jim Ketter
*Assistant Examiner* — Channing S Mahatan
(74) *Attorney, Agent, or Firm* — Holme Roberts & Owen LLP (57) ABSTRACT

Disclosed herein are a *Pichia pastoris*-derived auto-inducible NPS promoter; a recombinant expression vector carrying the promoter and a nucleotide sequence, the sequence being operably linked to the promoter and coding for a recombinant protein; a host cell transformed or transfected with the recombinant expression vector; and a method for producing a recombinant protein, comprising culturing the host cell to express the recombinant protein and isolating the protein. The NPS promoter allows a recombinant protein of interest to be produced on a large scale without the need of any inducer.

9 Claims, 7 Drawing Sheets

AUTO-INDUCIBLE SODIUM PHOSPHATE SYMPORTER PROMOTER FROM *PICHIA PASTORIS* AND METHOD FOR PRODUCING RECOMBINANT PROTEIN USING IT

CROSS REFERENCE TO RELATED APPLICATION

This application is a national stage application under 35 U.S.C. 371 of PCT Application No. PCT/KR2006/003096 having an international filing date of Aug. 7, 2006, which designated the United States, which PCT application claimed the benefit of Korean Application Serial No. 10-2006-0033064, filed Apr. 12, 2006, the entire disclosure of each of which is hereby incorporated herein by reference.

TECHNICAL FIELD

The present invention relates to an auto-inducible NPS promoter derived from *Pichia pastoris* and a method for producing recombinant proteins using the same. More particularly, the present invention relates to a *Pichia pastoris*-derived auto-inducible NPS promoter; a recombinant expression vector carrying the promoter and a nucleotide sequence, the sequence being operably linked to the promoter and coding for a recombinant protein; a host cell transformed or transfected with the recombinant expression vector; and a method for producing a recombinant protein, comprising culturing the host cell to express the recombinant protein and isolating the protein.

BACKGROUND ART

Protein synthesis is a multi-step process that begins with transcription, in which the genetic information encoded by DNA is transferred to an mRNA template. Transcription starts with the process of initiation. RNA polymerase binds to a specific region of DNA, called the promoter, which is usually located upstream of the gene to be transcribed. Many promoters, but by no means all, contain a common (conserved) sequence, called a consensus sequence.

In prokaryotes, the promoter consists of two short sequences at positions −10 and −35 upstream of the transcription start site. The sequence at −10 usually consists of the six nucleotides "TATAAT" (TATA box). The other sequence at −35 usually consists of the six nucleotides TTGACA. Most promoters differ from one another in the actual base sequence and distance from the transcription start site of the consensus sequence. This variability is believed to lead to different frequencies with which promoters initiate the transcription, that is, promoter strengths. The promoter is thus one of the important factors that determines the efficiency of protein production, and extensive research is being conducted to develop strong and specific promoters in various microorganisms.

*Pichia pastoris*, a species of methylotrophic yeast, is emerging as an important bio-model useful in the study of methanol metabolism and peroxisome production, and as a protein production host system superior to the conventional yeast, *Saccharomyces cerevisiae*. In addition, *Pichia pastoris* is recognized as a useful industrial resource that is useful in environmentally-friendly bio-processes thanks to its characteristic metabolism and physiological activity.

*Pichia pastoris* oxidizes methanol through formaldehyde and formate to carbon dioxide. These reactions are catalyzed by alcohol oxidase (AOX), formaldehyde dehydrogenase (FLD) and formate dehydrogenase (FMDH), respectively. *Pichia pastoris* has two alcohol oxidase genes (AOX1 and AOX2), which have respective inducible promoters. Thanks to this high activity, the AOX1 promoter is usually used to express a recombinant protein in yeast, while the AOX2 promoter (U.S. Pat. No. 5,032,516) is known to exhibit relatively weak activity (J. Tschopp et al. Nucleic Acids Res. 1987, vol. 15, pp. 3859-3876). In addition, an FLD gene promoter has been developed (D. Resina et al. Journal of Biotechnology, 2004, vol. 109, pp. 103-113). A glyceraldehyde-3-phosphate dehydrogenase (GAP) promoter, known as a strong constitutive promoter in various microorganisms, has also been developed for *Pichia pastoris* (Waterham et al. Gene, 1997, vol. 186, pp. 37-44).

Most frequently used in the production of recombinant proteins through *Pichia pastoris* are the promoters which are involved in methanol metabolism and are strongly induced by methanol. When using a promoter of a gene involved in methanol metabolism, care must be taken to avoid fire, because methanol, a highly combustible fuel, is required for transcription. In this case, the factory facility must include special instruments and is required to be carefully inspected. In addition, it is difficult to control the efficiency of protein expression with the GAP promoter. When having negative effects on the growth of the cell, other constitutive promoters are also difficult to use in the mass production of proteins because they cause cells to be instable.

Therefore, there is a need for a strong promoter that is inducible enough to regulate the expression of recombinant proteins at a desired time point suitable for the mass production or overexpression of proteins, and that requires for the induction thereof either an inducer that is not affected by the process, or no inducer at all.

DISCLOSURE OF INVENTION

Leading to the present invention, intensive and thorough research by the present inventors into the establishment of a protein production system free of the problems encountered in the conventional methods resulted in the finding that when a proper initial phosphorous concentration is decreased to a limited level as cells grow, the NPS promoter derived from *Pichia pastoris* in accordance with the present invention is automatically induced, without the need of any inducer, thus allowing a target protein to be produced effectively.

In accordance with an aspect thereof, the present invention provides a promoter, selected from a group consisting of: (1) a nucleotide sequence of SEQ ID NO.: 4; (2) a nucleotide sequence spanning from position 337 to position 1,044 of SEQ ID NO.: 4; (3) a nucleotide sequence spanning from position 571 to position 1,044 of SEQ ID NO.: 4; and (4) a nucleotide sequence spanning from position 743 to position 1,044 of SEQ ID NO.: 4.

In accordance with another aspect thereof, the present invention provides a recombinant expression vector, comprising the promoter and a nucleotide sequence, operably linked thereto, coding for a recombinant protein.

In accordance with a further aspect thereof, the present invention provides a host cell transformed or transfected with the recombinant expression vector.

In accordance with still a further aspect thereof, the present invention provides a method for producing a recombinant protein, comprising: culturing the host cell to express the recombinant protein; and isolating the recombinant protein from a culture.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

In accordance with an aspect thereof, the present invention pertains to a gene coding for $Na^+$-Phosphate Symporter (hereinafter referred to as "NPS") responsible for the transportation of phosphate. The NPS gene according to the present invention has the nucleotide sequence of SEQ ID NO: 1. This NPS gene can be synthesized chemically with reference to the sequence of SEQ ID NO:1, or by PCR using primers corresponding to predetermined regions at both ends of the gene, with the genomic DNA of *Pichia pastoris* serving as a template. Derived from *Pichia pastoris*, the NPS gene according to the present invention can be used as a probe for detecting NPS genes from *Pichia* spp.

In accordance with another aspect thereof, the present invention pertains to a promoter for regulating the expression of the NPS gene in *Pichia pastoris*. In an embodiment, the promoter of the NPS gene is composed of the nucleotide sequence of SEQ ID NO.: 4 (1,044 bp). Even part of the nucleotide sequence of SEQ ID NO.: 4, particularly, a TATA region or a CAT region, is found to have almost the same function as the promoter composed of the nucleotide of SEQ ID NO.: 4. In order to identify the minimum sequence necessary to function as an NPS gene promoter, various truncated promoter constructs were prepared, including sequences devoid of bases 1-336, 1-570, 1-742, 1-838, 1-891 and 1-921. These truncated promoter constructs were tested for the ability to allow the expression of a recombinant protein operably linked thereto. As a result, truncated constructs of the nucleotide sequence of SEQ ID NO.: 4 were observed to be able to express the recombinant protein when they were devoid of bases 1-336, 1-570 or 1-742, but were unable to do so when they were devoid of bases 1-838, 1-891 or 1-921.

Thus, the NPS gene promoter according to the present invention is selected from a group consisting of (1) a full-length nucleotide sequence of SEQ ID NO.: 4; (2) a nucleotide sequence spanning from position 337 to position 1044 of SEQ ID NO.: 4; (3) a nucleotide sequence spanning from position 571 to position 1044 of SEQ ID NO.: 4; and (4) a nucleotide sequence spanning from position 743 to position 1044 of SEQ ID NO.: 4. Preferably, the NPS gene promoter according to the present invention comprises a nucleotide sequence spanning from position 743 to position 1044 of SEQ ID NO.: 4, which is represented by SEQ ID NO.: 15.

These NPS gene promoters may be synthesized chemically, with reference to the nucleotide sequences disclosed in the present invention, or by PCR using primers corresponding to predetermined regions at both ends of each of the disclosed nucleotide sequences, with the genomic DNA of *Pichia pastoris* serving as a template. Since it is derived from *Pichia pastoris*, the NPS gene promoters according to the present invention can be utilized as probes for detecting the promoters of NPS genes of at least *Pichia* spp.

When cultured under phosphate-limited conditions, *Pichia pastoris* was observed to over-express the NPS gene (Example 1). In experiments for the expression of a reporter gene in conjugation with the NPS promoter, it was observed that, as phosphate was depleted from its initial concentration with the growth of cells, the NPS promoter was automatically induced, thus allowing the over-expression of the target protein even in the absence of any inducer (Example 4). When available phosphate becomes limited in a culture medium during the growth of cells, the NPS promoter is automatically induced, and thus strongly expresses a gene operably linked thereto. Therefore, the "NPS promoter" derived from *Pichia pastoris* can be used as an auto-inducible promoter.

A "promoter" is a regulatory region of DNA located upstream of a gene, recruiting RNA polymerase thereto so as to provide a control point for regulated gene transcription. Generally, promoters may be classified into two groups. Firstly, Activated in response to the presence of an inducer, an "inducible promoter" can promote the expression of a gene associated therewith. The use of inducible promoters in expressing genes requires the recruitment of inducers, which are generally expensive and may cause toxicity in the body or host cells in some cases. In addition, the use of an inducer entails various considerations for culturing, including the time point at which the inducer is fed, the concentration of the inducer in the culture media, etc. On the other hand, a "constitutive promoter" is an unregulated promoter that allows for the continual transcription of its associated gene, without the need of an inducer. However, the time point at which the gene is expressed cannot be controlled when using a constitutive promoter. Thus, when a target protein causes toxicity or a negative effect on the growth of host cells, it cannot be produced on a large scale. In contrast, an "auto-inducible promoter" enables its associated gene to be expressed at a desired time point, because its activation does not occur in response to the presence of an inducer. It is induced in response to the restriction of culture conditions or the depletion of a specific nutrient, thus overcoming the disadvantages of inducible promoters and constitutive promoters.

Thanks to the expression level of the NPS gene, the effect of the NPS gene promoter according to the present invention on the expression of its associated gene can be expected. In an embodiment, the expression level of the NPS gene can be quantitatively determined using an assay for the mRNA level thereof. Many RNA assay techniques are well known in the art. For example, RT-PCR, Northern blotting, hybridization, dot blot hybridization, DNA array hybridization, and/or DNA microbeads may be used.

Further, the NPS promoters according to the present invention are individually assayed for their ability to induce the expression of recombinant proteins. In an embodiment of the present invention, the expression of a reporter gene is under the control of the NPS promoters, and is quantitatively measured. Examples of the reporter gene suitable for this purpose include lacZ (β-galactosidase), uidA (β-glucuronidase), neo (neomycin phosphotransferase), cat (chloramphenicol acetyltransferase), dhfr (dihydrofolate reductase), aphIV (hygromycin phosphotransferase) and lux (luciferase). In the present invention, a fusion protein, in which a cellulose binding domain is linked to a lipase from *Bacillus stearothermophilus* (Ahn et al. Journal of Microbiol. Biotechnol. 2003, vol. 13, p. 451), is preferably used as a reporter. In addition to causing no cytotoxicity, the fusion protein has an advantage in that the lipase is secreted at high efficiency due to the cellulose binding domain, and can be measured for activity, thus reflecting the expression level of the fusion protein (Example 2).

The expressed reporter can be qualitatively or quantitatively analyzed using methods well known in the art. The methods, although dependent on reporter genes, preferably involve the use of antibodies binding specifically to corresponding reporter proteins or fragments thereof. Suitable antibodies may be monoclonal or polyclonal, and include acceptably modified antibodies or derivatives thereof, such as Fab fragments and single chain antibodies. For the identification and quantification of analytes through antigen-antibody reaction, agglutination assay, Western blotting, ELISA, RIA, enzyme immunoassay (EIA), fluorescent immunoassay (FIA), or immunoprecipitation may be employed.

As mentioned above, the NPS promoters according to the present invention allow for the strong expression of operably linked genes at desired time points, without the aid of any inducer, and thus can be used in the production of a recombinant protein. The term "recombinant protein" is intended to refer to a protein that is prepared through a genetic engineering technique, and is not limited to any particular one. Thus, the term "recombinant protein" is interchangeably used with the term "target protein".

The production of a recombinant protein must be preceded by the construction of a recombinant expression vector carrying an NPS promoter and a nucleotide sequence, operably linked thereto, coding for the recombinant protein. The recombinant expression vector constitutes an aspect of the present invention. The recombinant expression may be prepared from a commercially available vector. In this case, the promoter originally existing in the vector may be replaced with the NPS promoter according to the present invention. In addition, the recombinant vector may be designed to contain the NPS promoter according to the present invention in combination with typically used regulatory sequences.

As used herein, the term "vector" means a vehicle functioning to stably deliver the nucleic acid sequence of a recombinant protein into a host cell. To be useful, a vector must have the ability to replicate by itself and to be transformed into host cells, and must include a detectable portion.

The term "recombinant expression vector", as used herein, is intended to refer to a circular DNA molecule that is used to introduce and express a specific operably linked gene into a host cell. In order to increase the expression level of a heterogeneous gene introduced into a host cell, as is well known in the art, the gene must be operably linked to transcriptional and translational regulatory sequences that can function in the host cell. Preferably, the gene of interest is carried by one vector containing a regulatory sequence, a selectable marker, and a replication origin together.

The term "regulatory sequence", as used herein, means a nucleotide sequence necessary or helpful for the expression of a recombinant protein. Examples of the regulatory sequence include secretion signals, polyadenylation signals, propeptide sequences, enhancers, upstream activation sequences, and transcription termination factors. In the present invention, the regulatory sequence comprises at least a promoter, and preferably a promoter and a secretion signal. Optionally, the regulatory sequence may comprise other regulatory factors in order to increase the expression level of a target protein.

The term "secretion signal", as used herein, is intended to refer to an amino acid sequence that allows an expressed protein to be transported outside the cell, and is usually employed to facilitate the isolation and purification of the recombinant protein. Surface proteins or secreted proteins that are transferred outside cells have N-terminal sequences which are cleaved by signal peptidase in cellular membranes. Examples of secretion sequences useful in the present invention include, but are not limited to, an α-factor signal sequence, a killer toxin leader signal sequence, an invertase signal sequence, and an α-amylase signal sequence.

In order to be expressed, a nucleotide sequence coding for a recombinant protein must be operably linked to the regulatory sequence including the promoter according to the present invention. By the term "operably linked", as used herein, it is meant that one nucleotide sequence is functionally arranged with another nucleotide sequence. For example, if it participates in the secretion of a mature protein, a secretion sequence is operably linked to the protein. If the transcription of a coding sequence is under the control of a promoter, it is operably linked to the promoter. If a ribosome-binding site is placed at a position that allows a coding sequence to be translated, it is operably linked to the coding sequence. Typically, an "operably linked" DNA sequence is in contact with another sequence. For example, a secretory leader is in contact with a target gene, and exists within an open reading frame. However, an enhancer does not need contact with a target gene.

A host cell transformed or transfected with the recombinant expression vector constitutes another aspect of the present invention. Examples of the host cell useful in the present invention include typical eukaryotic and prokaryotic hosts, such as *E. coli, Pseudomonas* spp., *Bacillus* spp., *Streptomyces* spp., fungi and yeasts, insect cells, such as *Spodoptera frugiperda* (SF9), animal cells, such as CHO and mouse cells, African green monkey cells, such as COS 1, COS 7, BSC 1, BSC 40 and BMT 10, cultured human cells, and plant cells. Yeasts are preferably host cells in the present invention. More preferable is *Pichia pastoris*, because it has the same origin as the NPS promoter of the present invention.

Transformation or transfection may be carried out according to the techniques disclosed by Davis et al., in Basic Methods in Molecular Biology, 198. Preferable examples include DEAE-dextran mediated transfection, electroporation, transduction, calcium phosphate transfection, cationic lipid-mediated transfection, scrape loading, and infection.

In accordance with another aspect thereof, the present invention pertains to a method for producing a recombinant protein, comprising culturing the transfected or transformed cell to express the recombinant protein and isolating the recombinant protein.

According to a typical technique, the host cell of the present invention may be cultured in a nutrient medium suitable for the production of a recombinant protein, for example, a medium containing phosphorus at a concentration of 0.001-0.02 mM of phosphorus in an early stage (initial culture stage). For instance, host cells may be cultured in a laboratory or an industrial fermentor through small or large scale fermentation or shaking flask fermentation under conditions allowing a target protein to be expressed and/or isolated. Culture is performed in a suitable nutrient medium containing a carbon source, a nitrogen source and inorganic salts using a well known technique. A culture medium may be a commercially available one, or may be prepared with reference to the ingredients and compositions disclosed in the catalog of the American Type Culture Collection. The host cell of the present invention may be subjected to batch culture or fed-batch culture.

The term "batch culture", as used herein, means a biological batch process that uses a culture medium to which all of the nutrients necessary for growth are added once in an initial stage. In a batch culture, the host cell can grow either until the medium is depleted of one of the necessary nutrients or until conditions unsuitable for the growth thereof are formed (for example, the pH is lowered, thus inhibiting the growth of host cells).

The term "fed-batch culture", as used herein, means a biological batch process which is based on the feeding of one or more growth nutrient substrates to a culture just after the start of fermentation, or after the culture reaches a predetermined stage or is depleted of the nutrient substrates. In a fed-batch process for example, the pH is adjusted to a predetermined value, and at least one growth nutrient is further fed to a culture. The host cells will grow at a rate depending on the nutrient feeding rate. Generally, a single nutrient or a carbon source is a growth limiting factor. Also, other nutrients or conditions may be used as limiting factors. For example, the growth of host cells may be limited by a nitrogen source, oxygen, or specific nutrients, such as vitamins or amino acids (when the host cells are auxotrophic therefor).

From the culture, a recombinant protein may be isolated using a method that is well known in the art. For example, the isolation of a recombinant protein from the culture can be achieved by, but is not limited to, conventional methods, such as centrifugation, filtration, extraction, spray drying, evaporation and precipitation. Further, various techniques, including chromatography (e.g., ion exchange, affinity, hydrophobic and size extrusion), electrophoresis, fractional crystallization (e.g., ammonium sulfate precipitation), SDS-PAGE and extraction may be used in the purification of the recombinant protein.

A better understanding of the present invention may be obtained through the following examples which are set forth to illustrate, but are not to be construed as the limit of the present invention.

EXAMPLE 1

Cloning of *Pichia pastoris*-Derived NPS Promoter

In order to screen genes that can be over-expressed in *Pichia pastoris* under phosphorus-limited conditions, it was cultured in a continuous manner in a phosphorus-limited medium according to the method disclosed in Korean Pat. Appl'n No. 2004-98303, filed by the present applicant on Nov. 27, 2004. The mRNA isolated from the cell mass thus cultured was used as a substrate for RT-PCR to allow for a bank of overexpressed genes. The bank of these genes was found to have a $Na^+$-phosphate symporter (NPS) gene, responsible for the metabolism of phosphorus, through nucleotide sequencing.

Then, a promoter for regulating the expression of the gene was cloned. In this regard, reverse PCR was conducted in the presence of synthetic primers (SEQ ID NO.: 2 and SEQ ID NO.: 3), with the previously cloned $Na^+$-phosphate symporter (NPS) gene serving as a probe. The genomic DNA of *Pichia pastoris* was used as a template for the reverse PCR after being digested with various restriction enzymes. From the genomic DNA fragments obtained after digestion with KpnI, a gene coding for $Na^+$-phosphate symporter (NPS) was detected through reverse PCR. This NPS gene was cloned in a pSTBlue-1 vector, and the recombinant vector thus formed was named "pST1". Through base sequencing, an open reading frame of NPS and its upstream region, that is, a promoter 1,044 by long (SEQ ID NO.: 4), were revealed. This promoter was designated "$P_{NPS}$".

Figure 1:
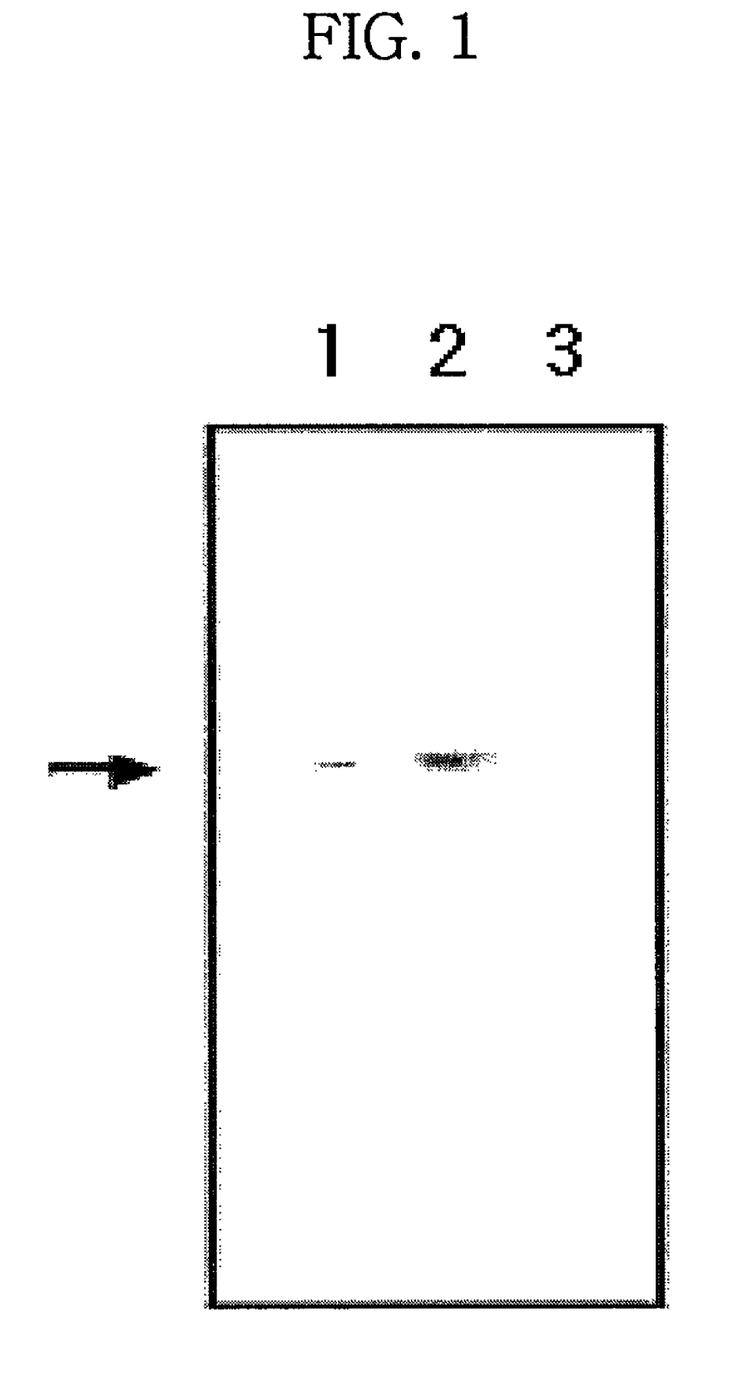
FIG. 1 shows the result of Northern blotting with an NPS gene against the mRNA from *Pichia pastoris* cultured in phosphorus-limited media (the cells growing at a specific growth rate of 0.14 (1), 0.08 (2) and 0.03 (3))

The overexpression of the gene under a phosphorus limited condition was observed through the Northern blotting of the NPS gene with the mRNA isolated from the cells cultured under phosphorus-limited conditions (FIG. 1).

EXAMPLE 2

Construction of Recombinant Expression Vector Carrying the Promoter $P_{NPS}$

A lipase gene was used as a reporter gene to verify the activity of the cloned promoter $P_{NPS}$. In detail, lipase L1F (CBD-L1-Lipase), in which a gene coding for a cellulose binding domain is linked to a lipase, was used as a reporter gene because it can more stably express lipase L1 (Aim et al. Journal of Microbiol. Biotechnol. 2003, vol. 13, p. 451). A recombinant expression vector carrying a lipase gene and the promoter $P_{NPS}$ was based on a pPIC9 vector (Invitrogen, U.S.A.).

Figure 2:
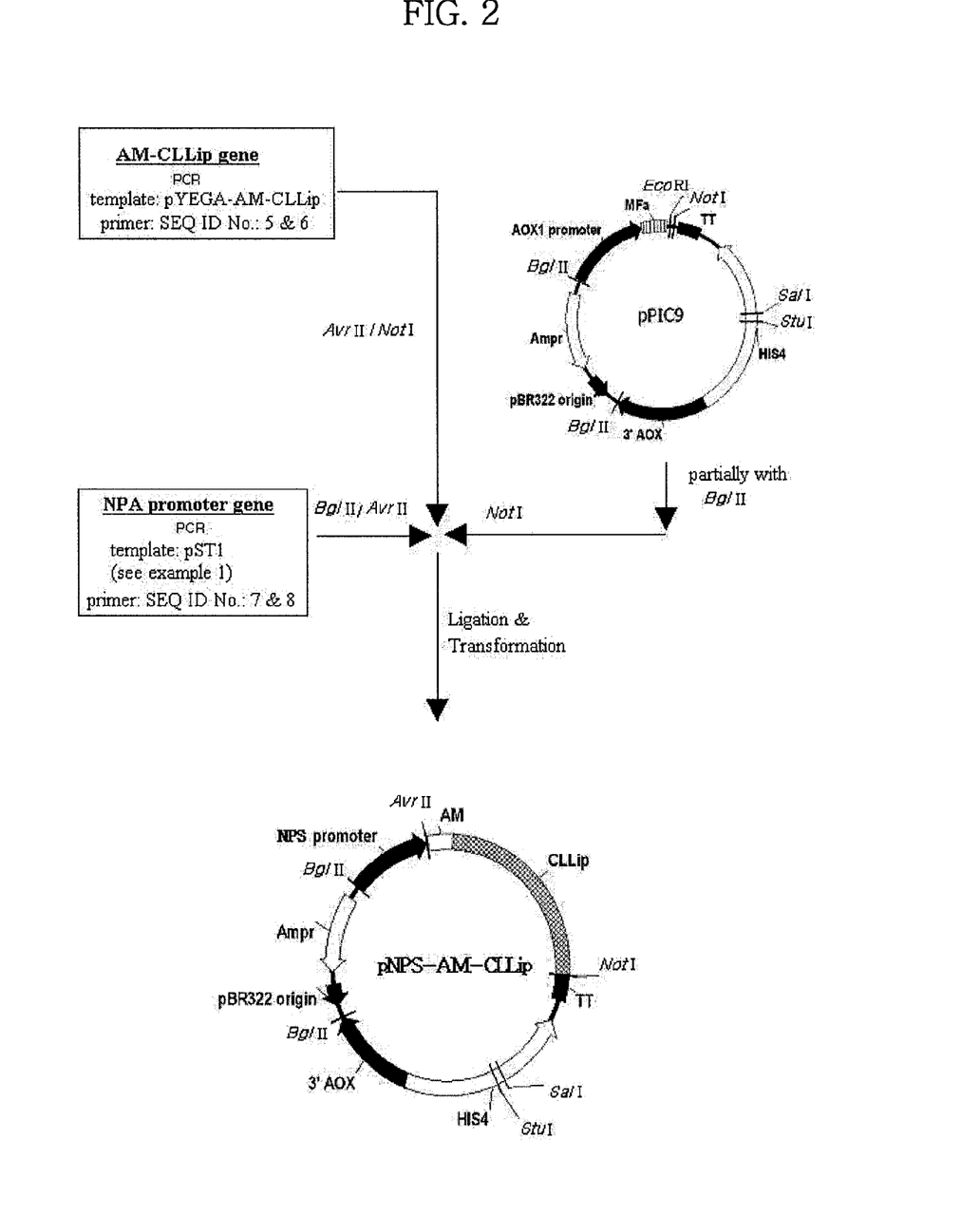
FIG. 2 is a schematic diagram showing the construction of the recombinant expression vector pNPS-AM-CLLip, comprising a *Pichia pastoris*-derived NPS gene and a reporter gene operably linked thereto.

With reference to FIG. 2, a method of preparing a recombinant expression vector carrying a lipase reporter gene and the promoter $P_{NPS}$ is illustrated. A sequence containing α-amylase-derived secretion signal and lipase was amplified from pYEGA-AM-CLLip (Ahn et al. Journal of Microbial. Biotechnol. 2003, vol. 13, p. 451) by PCR in the presence of synthetic primers of SEQ ID NO.: 5 and SEQ ID NO.: 6 (respectively containing AvrII and NotI restriction sites). Also, the promoter $P_{NPS}$ was amplified by PCR while the pST1, cloned in Example 1, served as a template in the presence of synthetic primers of SEQ ID NO.: 7 and SEQ ID NO.: 8 (respectively containing BglII and AvrII restriction enzyme sites). The gene, coding for α-amylase-derived secretion signal and lipase, was digested with AvrII and Nod while the promoter $P_{NPS}$ was treated with BglII and AvrII. Subsequently, the reporter gene coding for α-amylase-derived secretion signal and lipase and the promoter $P_{NPS}$ were ligated to a pPIC9 vector, which was partially digested with BO and NotI. As a result, a recombinant expression vector carrying the promoter $P_{NPS}$ and genes coding for α-amylase and lipase was prepared and designated "pNPS-AM-CLLip". When expressed from the vector, the α-amylase serves as a secretion signal to secrete the lipase extracellularly.

EXAMPLE 3

Transformation of *Pichia pastoris*

*Pichia pastoris* GS115 was transformed with the recombinant expression vector pNPS-AM-CLLip prepared in Example 2. The expression vector prepared in Example 2 was inserted into a his4 gene on the genome of *Pichia pastoris* GS115. For this, the recombinant expression vector was digested with BspEI, which is also present in the his4 gene, and then transformed into *Pichia pastoris* using a lithium/TE method (Hill et al. Nucl. Acids. Res. 1991, vol. 19, p. 5791). In detail, the recombinant expression vector digested with BsPEI, a carrier DNA and PEG/LiAc were mixed and allowed to react at 30° C. for 30 min. Then, the addition of DMSO was followed by reaction at 42° C. for 15 min. After centrifugation, the pellet was suspended in 200 μl of TE buffer. The suspension was spread over an His (−) plate (glucose 2%, yeast nitrogen base 0.67%, an amino acid mix without his 0.077%, agar 2%) before culturing for 2-3 days. From the transformants thus obtained, a transformant that had only a single copy of the recombinant expression vector inserted into the genome was selected.

EXAMPLE 4

Expression of Lipase Under the Control of $P_{NPS}$

The reporter gene was utilized to observe the effect of the promoter $P_{NPS}$ on the expression pattern thereof according to phosphorus concentrations.

In more detail, the *Pichia pastoris* transformed with pNPS-AM-CLLip, selected in Example 3, was cultured in a batch type in media containing different initial phosphorus concentrations (adjusted with $NaH_2PO_4 \cdot 2H_2O$), as shown in Table 1, below. The cultures from cell mass were removed and analyzed for lipase level.

Dried weights of cell mass, lipase activity, and concentrations of glucose, glycerol and phosphorus were measured according to the time period of culture. The measurement was carried out as follows.

(1) Dry weight of cell mass: A cell pellet obtained through the centrifugation of a cell culture was washed with isotonic buffer, dried at 80° C., and weighed.
(2) Lipase activity: The titer of lipase was measured using a pH-stat method.
(3) Glucose level: Glucose was quantitatively assayed using a glucose analyzer.

Phosphorus level: Phosphorus was quantitatively assayed using the method of Fiske-Shubbarow (Fiske et al., Journal of Biological Chemistry, 1925, vol. 66, p. 375).

TABLE 1

| Ingredients | Composition of Media Used in Batch Type | | |
|---|---|---|---|
| | Culture A (g/L) | Culture B (g/L) | Culture C (g/L) |
| Glucose | 50 | 50 | 50 |
| $MgSO_4 \cdot 7H_2O$ | 3 | 3 | 3 |
| $(NH_4)_2SO_4$ | 15 | 15 | 15 |
| $K_2SO_4$ | 4.55 | 4.55 | 4.55 |
| KOH | 1.03 | 1.03 | 1.03 |
| $CaCl_2$ | 0.3 | 0.3 | 0.3 |
| $NaH_2PO_4 \cdot 2H_2O$ | 0.025 | 0.25 | 2.5 |
| Trace elements | 2 mL | 2 mL | 2 mL |

Figure 3A:
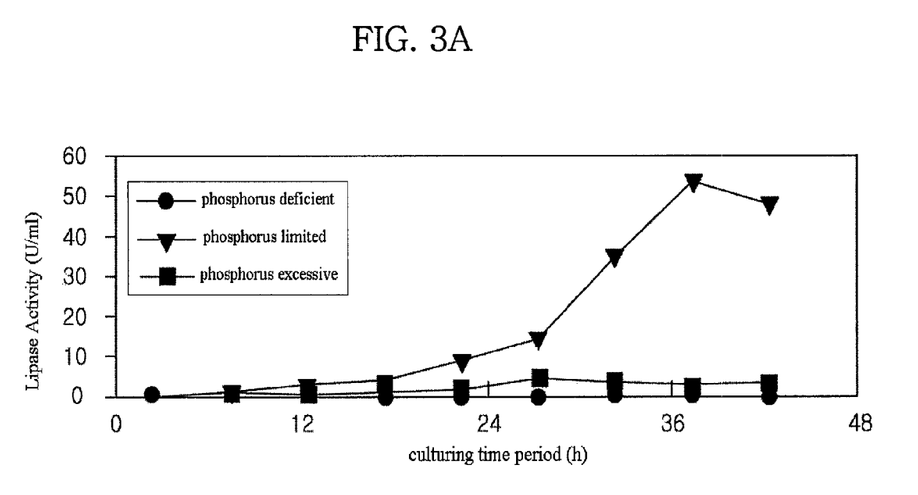
FIG. 3A is a graph in which the lipase activity of cell cultures was plotted against the culture time period when the *Pichia pastoris* transformed with pNPS-AM-CLLip was cultured as a batch type, in media containing different initial phosphorus contents (●: phosphorus-deficient, ▼: phosphorus-limited, ■: excessive phosphorus)
Figure 3B:
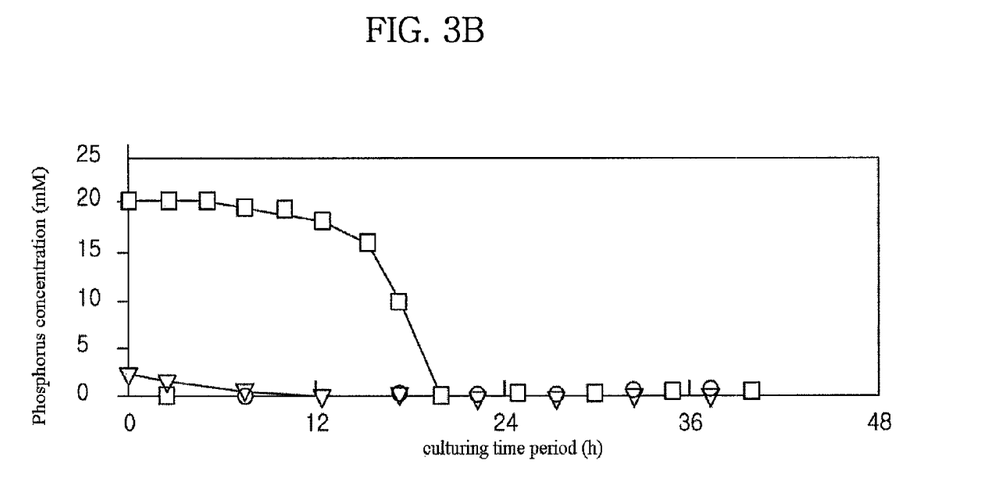
FIG. 3B is a graph in which the phosphorus concentrations of cell cultures were plotted against the culture time period when the *Pichia pastoris* transformed with pNPS-AM-CLLip was cultured as a batch type, in media containing different initial phosphorus contents (○: phosphorus-deficient, ▽: phosphorus-limited, □: excessive phosphorus)
Figure 3C:
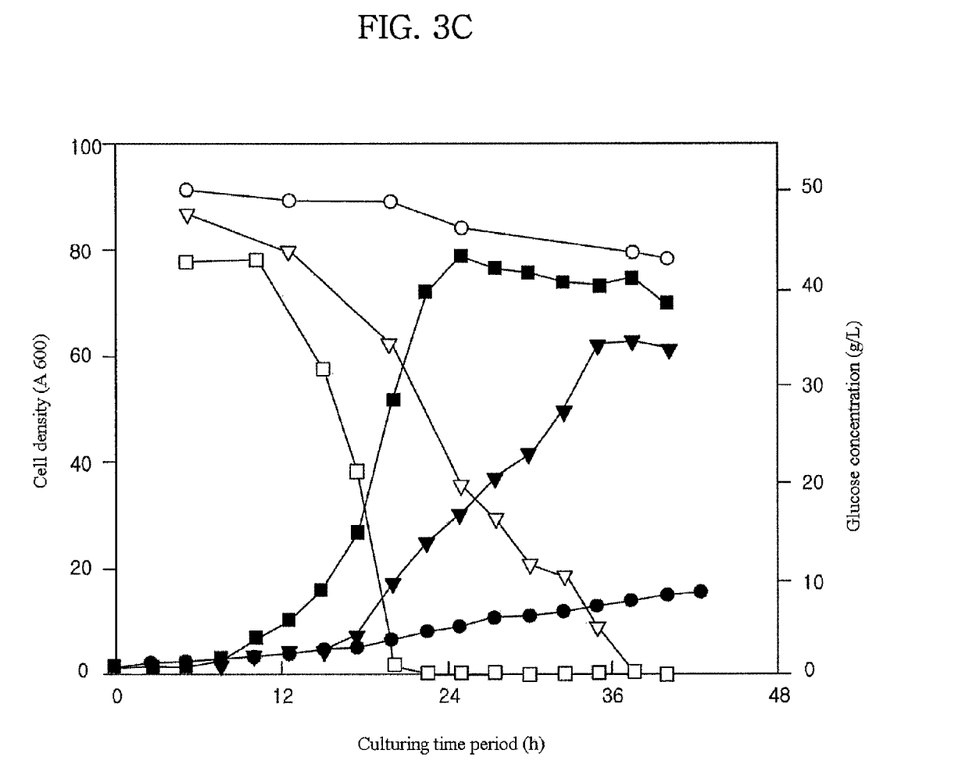
FIG. 3C is a graph in which glucose concentration and cell density were plotted against the culture time period when the *Pichia pastoris* transformed with pNPS-AM-CLLip was cultured as a batch type, in media containing different initial phosphorus contents [glucose concentration-○: phosphate depleted, ▽: phosphorus-limited, □: excessive phosphorus), cell density-(●: phosphorus-deficient, ▼: phosphorus-limited, ■: excessive phosphorus)].

With reference to FIGS. 3A, 3B and 3C, lipase activity, phosphorus concentration, cell density and glucose concentration were plotted against the time period of culture when the *Pichia pastoris*, transformed with pNPS-AM-CLLip, was cultured as a batch type in media containing different initial phosphorus contents.

As seen in the plots, higher initial concentrations of phosphorus in culture media resulted in higher cell growth rates and glucose intake rates. In Culture C, containing an initial phosphorus concentration of 20 mM (excessive phosphorus), cells were grown to the extent of 70 O.D. with glucose 50 g/L completely depleted within 22 hours after the initiation of culturing. In Culture B, containing an initial phosphorus concentration of 2.0 mM (limited phosphorus), cells were grown to 61 O.D. while all of the initial amount of glucose of 50 g/L was completely consumed 37.5 hours after the initiation of culture. Culture A, containing an initial phosphorus concentration of 0.20 mM (phosphorus depleted), was measured to have 43 g/L of glucose even after culturing for 40 hours, with the cells grown up to 15 O.D. These data indicate that the concentration of phosphorus has an influence on the growth of the cell. Culture C showed a low concentration of phosphorus only at the end of log-phase growth, indicating that the growth of cells was not limited by phosphorus. In Culture B, the growth of cells is limited from 12 hours after the initiation of culturing. Because it was initially supplied with a very low amount of phosphorus, Culture A allowed the cells to grow only at a limited rate.

Figure 4:
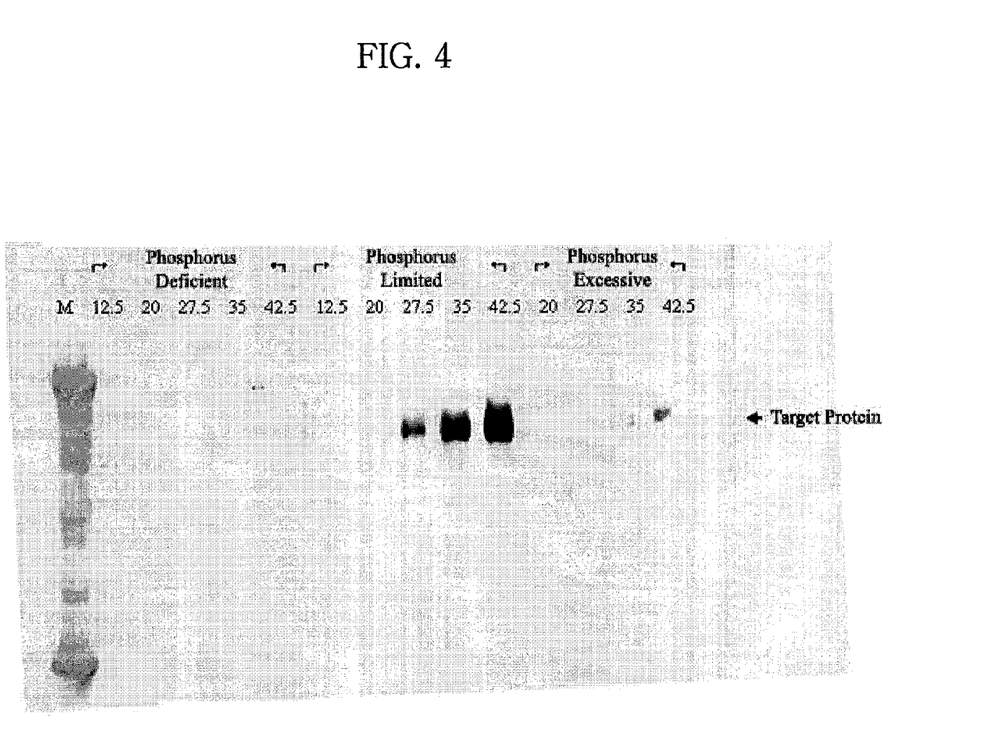
FIG. 4 is a result of Western blotting against the lipase protein obtained from pNPS-AM-CLLip-transformed *Pichia pastoris* cultured in media containing different initial phosphorus contents.

Lipase activity was observed in Culture B, whereas almost no lipase activity was detected in Culture A and Culture C. This is proven by the Western blotting results of FIG. 4. Therefore, when the concentration of phosphorus decreases to a limited level from a proper initial level as the cells consume phosphorus for their growth, the NPS promoter according to the promoter is automatically induced, thus allowing an operably linked protein to be produced. In contrast, when the concentration of phosphorus is so rich that the cells are not limited by phosphorus, or is too low for the cells to grow, the target protein was not produced. Consequently, the NPS promoter according to the present invention is auto-inducible, and thus it can be controlled with the concentration of phosphorus, and is expressed under phosphorus-limited conditions without the need of any inducer.

EXAMPLE 5

Screening of NPS Promoter for Essential Control Region

In order to identify the regions thereof which play an essential role in transcription, the previously cloned $P_{NPS}$ (SEQ ID NO.: 4) 1,044 by long were truncated from the 5'-end to predetermined points, and the promoter fragments thus formed were linked to the lipase gene, serving as a reporter gene, as in the pNPS-AM-CLLip vector of Example 2.

In detail, nucleotide fragments of the promoter $P_{NPS}$ (SEQ ID NO.: 4), which are devoid of regions spanning from position 1 to positions 336, 570, 742, 838, 891 and 921, were prepared by PCR using sets of primers of SEQ ID NOS.: 9 and 8, SEQ ID NOS.: 10 and 8, SEQ ID NOS.: 11 and 8, SEQ ID NOS.: 12 and 8, SEQ ID NOS.: 13 and 8, and SEQ ID NOS.: 14 and 8, with the pNPS-AM-CLLip serving as a template. The PCR products thus obtained were digested with BglII and AvrII and individually ligated to the pNPS-AM-CLLip, which was previously digested with BglII and AvrII. The resulting recombinant expression vectors were designated pNPS(Δ336)-AM-CLLip, pNPS(Δ570)-AM-CLLip, pNPS (Δ742)-AM-CLLip, pNPS(Δ838)-AM-CLLip, pNPS (Δ891)-AM-CLLip, and pNPS(Δ921)-AM-CLLip, respectively. These expression vectors were transformed into *Pichia pastoris* GS115, as described in Example 3, and transformants that had only a single copy of each recombinant expression vector inserted respectively into the genomes thereof were selected.

Figure 5:
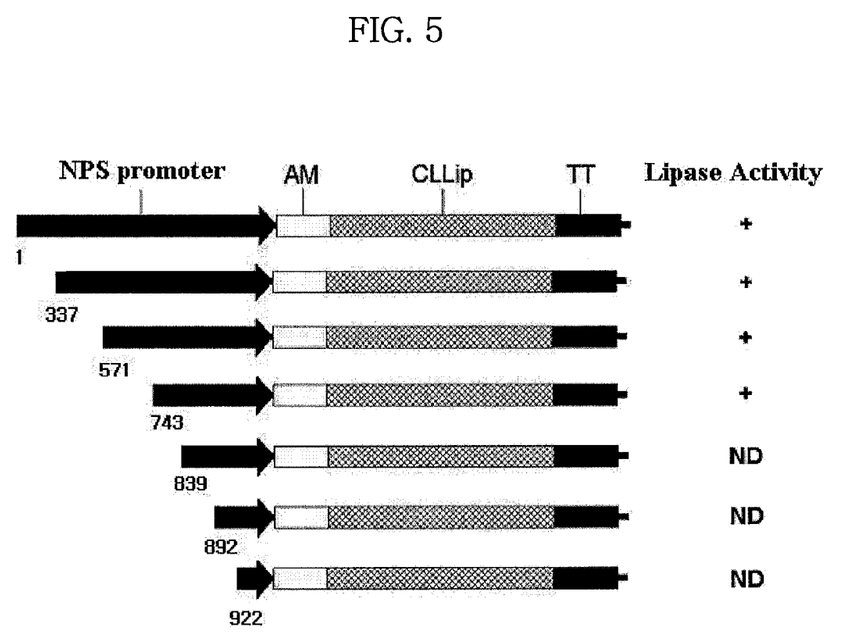
FIG. 5 is a schematic diagram illustrating a strategy for screening a minimum nucleotide sequence essential for the biological function of the NPS promoter (+: positive lipase activity, ND: lipase activity not detected).

In order to examine whether the truncated promoters are active, the selected transformants were cultured on plates which allowed halos to form with the activity of the lipase. As seen in FIG. 5, the *Pichia pastoris* strains transformed respectively with pNPS(Δ336)-AM-CLLip, pNPS(Δ570)-AM-CLLip and pNPS(Δ742)-AM-CLLip were observed to have similar lipase activities, while no activity was detected in the *Pichia pastoris* transformed with pNPS(Δ838)-AM-CLLip, pNPS(Δ891)-AM-CLLip or pNPS(Δ921)-AM-CLLip. Therefore, the region spanning from the 3'-end to a length of 302 by in the direction of the 5'-end is essentially responsible for the function of $P_{NPS}$ of SEQ ID NO.: 4. This essential part of the promoter $P_{NPS}$ is represented by SEQ ID NO.: 15.

INDUSTRIAL APPLICABILITY

When a proper initial phosphorous concentration is decreased to a limited level as cells grow, the NPS promoter derived from *Pichia pastoris* in accordance with the present invention is automatically induced, thus allowing a target protein to be produced effectively. An inducible or constitutive expression system taking advantage of the auto-inducible NPS promoter according to the present invention can be a promising solution to the stability problem of cell strains and other problems, from which conventional processes of producing recombinant proteins on a mass scale suffer.

While this invention has been described in connection with what is presently considered to be the most practical and preferred embodiment, it is to be understood that the invention is not limited to the disclosed embodiment and the drawings thereof, but, on the contrary, is intended to cover various modifications and variations within the spirit and scope of the appended claims.

The invention claimed is:

1. A promoter, selected from the group consisting of:
   (1) an isolated nucleotide sequence of SEQ ID NO.:4
   (2) an isolated nucleotide sequence spanning from position 337 to position 1,044 of SEQ ID NO.:4
   (3) an isolated nucleotide sequence spanning from position 571 to position 1,044 of SEQ ID NO.:4 and
   (4) an isolated nucleotide sequence spanning from position 743 to position 1,044 of SEQ ID NO.:4.

2. A recombinant expression vector, comprising the promoter of claim 1 and an isolated nucleotide sequence, operably linked thereto, coding for a recombinant protein.

3. A host cell transformed or transfected with the recombinant expression vector of claim 2.

4. The host cell according to claim 3, which is a yeast.

5. The host cell according to claim 4, which is *Pichia pastoris*.

6. A method for producing a recombinant protein, comprising: culturing the host cell of claim 4 to express the recombinant protein; and isolating the recombinant protein from a culture.

7. A method for producing a recombinant protein, comprising: culturing the host cell of claim 5 to express the recombinant protein; and isolating the recombinant protein from a culture.

8. A method for producing a recombinant protein, comprising:
   culturing the host cell of claim 3 to express the recombinant protein; and
   isolating the recombinant protein from a culture.

9. The method according to claim 6, wherein the host cell is cultured in a medium containing phosphorus at a concentration of 1 to 20 mM.

* * * * *

SEQUENCE LISTING

```
<160> NUMBER OF SEQ ID NOS: 15

<210> SEQ ID NO 1
<211> LENGTH: 732
<212> TYPE: DNA
<213> ORGANISM: Pichia pastoris
<220> FEATURE:
<221> NAME/KEY: gene
<222> LOCATION: (1)..(732)

<400> SEQUENCE: 1
atgagtttgg ttgcacttca tcaattcgac tacatctttg cgatcgccat gatgtttgca      60
ttcttggatg cattcaacat cggcgcaaat gatgtagcaa actccttttc ttcatcagtc     120
tcctcgagat gtctgaaata ctggcaagcg atgatcttag ctgccatcat ggaattttg      180 ggtgccgtct tagctggtgc ccgtgtcact gacactatta gaaagagaat tatcaacgtt     240
cacgctttcg acgacgaccc agccatgctg atgttgacca tggccactgc cttggtcggt     300
tcttctgtct ggttgagtat tgccacttat gtcagagctc ctgtctccac cactcattcc     360
attgttggtg gtgtcattgg tgctggtatc gctgctaaag gtgctggtga gatccactgg     420
ggatggagtg gatttgccaa gattgttgct tcttggttca tcgctccatg tgttgctggt     480
ggattcgctt ccgtcctttt cctcttctgt aagttctcaa ttttggagag aaagcatgat     540
gccagaaatg ccccttctgt tgctccatgt atcgtcttct tgacttttgc tgtcctgaca     600
atgttgatcg tctggaaggg agctccaaac ttgaacttgg acgacctttc tactggtgct     660
accgtcggnt ctatcttcgg tgttgctggt gttgctacaa tcatttacat cacattcttt     720
ttccattctt ga                                                        732

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gaatacacac aagcatctat ttgag                                           25

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
```

```
ccactccatc cccagtggat ctcacc                                          26
```

<210> SEQ ID NO 4
<211> LENGTH: 1044
<212> TYPE: DNA
<213> ORGANISM: Pichia pastoris
<220> FEATURE:
<221> NAME/KEY: promoter
<222> LOCATION: (1)..(1044)

<400> SEQUENCE: 4

```
aaagtcagcg gaatgtttga acagggtcca tctgagaaag aggagccagc acaggaatcg     60
gtggtaataa acgaactcat ggaaaaagca cagtccaggc ctgaaaagcc acccaaaaga   120
ctggcagagt tggaggaaat ctgggtggat ggtttgcaaa agaaatacgg taacgactat   180
gaaagaatga atgggatcg caaactgaac cccatgatgc taacgccccg caagttggag   240
aaactgtttg aaaggaaatt gcaggtcgaa gattacgaca aagacatac agcatgatta   300
ggtcacacgg cttgtcgttt ttctttcttt tttttaccca cgtagaagga ttatagggac   360
tgaactgaca tgacatgtga ctgtaacaga taggtaagta aggcacataa tttaagtgac   420
agtgtcaaca atgccaattt ttttttttt acaacaatgc ccacgttgtt accgatgctc   480
gcacgtagat tcctttactg gccaagaact tggcgcgaaa tgtgatatcg attgaatctg   540
ataaaagaaa caaaaaaaaa aaaatttat ccggtgtagg gatgtgacta aacgcctcgt   600
gtgacaacgt gggtggtatc tttccttcgc cacgtgcgcg tgcaacctat tgtatggcta   660
aattaaaggg ccatgtcaaa gacccttaaa cccttgataa tagcaaagac tggggaagca   720
ggccctgaaa agacagaaca atcagaattc tctaatttcc tccaccgag agccgtccaa   780
tggcatagat tacctcgtta aacgaaattc gaaagctcaa tttccaaata cccactttcc   840
ttttcgatcc ttattgctgc tggacctact ctccaaagtc ttggcaaggc acatgtctc    900
aattttaat tgaaaaccgt tagaaagtga agccgacttt aggtataaat agtaggaacc   960
ccagcaggca gagctgatca cttgtaaacc tttctctgat acacacaagc atctatttga  1020
gtactcatct tataatcatt caca                                          1044
```

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5

```
gcagctagga tgatggtcgc gtggtgg                                        27
```

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6

```
gcagcggccg caagctttta aggccgcaaa ctcgc                               35
```

<210> SEQ ID NO 7
<211> LENGTH: 29
<212> TYPE: DNA
<213> ORGANISM: Artificial Sequence
<220> FEATURE:

<223> OTHER INFORMATION: primer

<400> SEQUENCE: 7
agatctggag ccagcacagg aatcggtgg                                    29

<210> SEQ ID NO 8
<211> LENGTH: 35
<212> TYPE: DNA
<213> ORGANISM: Artificial Sequence
<220> FEATURE:
<223> OTHER INFORMATION: promoter

<400> SEQUENCE: 8
gcagctaggt gtgaatgatt ataagatgag tcatc                             35

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
tcaagatctc ccacgtagaa ggattatagg gac                               33

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
tcaagatctc cggtgtaggg atgtgactaa acgcc                             35

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
tcaagatctc agaattctct aatttcctcc acc                               33

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
tcaagatctc cttttcgatc cttattgctg c                                 31

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
tcaagatcta catgtctcaa ttttttaattg                                  30

<210> SEQ ID NO 14

```
<211> LENGTH: 31
<212> TYPE: DNA
<213> ORGANISM: Artificial Sequence
<220> FEATURE:
<223> OTHER INFORMATION: primer

<400> SEQUENCE: 14
tcaagatcta gaaagtgaag ccgactttag g                               31

<210> SEQ ID NO 15
<211> LENGTH: 302
<212> TYPE: DNA
<213> ORGANISM: Pichia pastoris
<220> FEATURE:
<221> NAME/KEY: promoter
<222> LOCATION: (1)..(302)

<400> SEQUENCE: 15
cagaattctc taatttcctc caccagagag ccgtccaatg gcatagatta cctcgttaaa    60
cgaaattcga aagctcaatt tccaaatacc cactttcctt ttcgatcctt attgctgctg   120
gacctactct ccaaagtctt ggcaaggcca catgtctcaa tttttaattg aaaaccgtta   180
gaaagtgaag ccgactttag gtataaatag taggaacccc agcaggcaga gctgatcact   240
tgtaaacctt tctctgatac acacaagcat ctatttgagt actcatctta taatcattca   300
ca                                                                  302
```